(12) United States Patent
Swift

(10) Patent No.: US 8,366,441 B2
(45) Date of Patent: Feb. 5, 2013

(54) AIR/LIGHT DENTAL DEVICE

(76) Inventor: Mary K. Swift, Dallas, TX (US)

( * ) Notice: Subject to any disclaimer, the term of this patent is extended or adjusted under 35 U.S.C. 154(b) by 234 days.

(21) Appl. No.: 12/350,207

(22) Filed: Jan. 7, 2009

(65) Prior Publication Data

US 2009/0176186 A1 Jul. 9, 2009

Related U.S. Application Data

(60) Provisional application No. 61/010,150, filed on Jan. 7, 2008.

(51) Int. Cl.
*A61C 1/00* (2006.01)
(52) U.S. Cl. .......................................................... 433/29
(58) Field of Classification Search .................... 433/29, 433/32, 80; 606/2, 13, 14, 25; 600/245, 600/246
See application file for complete search history.

(56) References Cited

U.S. PATENT DOCUMENTS

| | | | | |
|---|---|---|---|---|
| 4,826,431 | A * | 5/1989 | Fujimura et al. | 433/29 |
| 5,147,203 | A * | 9/1992 | Seidenberg | 433/29 |
| 5,297,962 | A * | 3/1994 | O'Connor et al. | 433/89 |
| 6,663,386 | B1 * | 12/2003 | Moelsgaard | 433/29 |
| 6,991,356 | B2 | 1/2006 | Tsimerman et al. | |
| 6,991,456 | B2 | 1/2006 | Plank | |
| 6,994,546 | B2 | 2/2006 | Fischer et al. | |
| 7,182,597 | B2 | 2/2007 | Gill et al. | |
| 2005/0196721 | A1 | 9/2005 | Jackson, III et al. | |
| 2006/0024638 | A1 * | 2/2006 | Rosenblood et al. | 433/29 |
| 2008/0118887 | A1 * | 5/2008 | Teufelberger et al. | 433/29 |

* cited by examiner

*Primary Examiner* — Sunil K Singh
(74) *Attorney, Agent, or Firm* — Jeffrey G. Degenfelder; Carstens & Cahoon, LLP

(57) ABSTRACT

A hand held curing light device having an integral, self-contained compressed-air system, which allows the operator to complete a procedure involving the use of light-curable compounds using a single hand-held instrument.

10 Claims, 4 Drawing Sheets

AIR/LIGHT DENTAL DEVICE

CROSS-REFERENCE TO RELATED APPLICATION

This application claims the benefit of and priority to a U.S. Provisional Patent Application No. 61/010,150 filed Jan. 7, 2008, the technical disclosure of which is hereby incorporated herein by reference.

BACKGROUND OF THE INVENTION

1. Technical Field of the Invention

The present invention relates to light generating instruments for curing light-curable compounds, such as those utilized in dental applications. More particularly, the present invention relates to curing fight instruments having an integral compressed-air delivery system, which is used to dry the treatment area and spread the adhesive compounds.

2. Description of the Related Art

Light-curable compounds, such as adhesives and bonding or filling compounds, are widely used in dental applications to attach objects to surfaces or to fill gaps or other openings, such as a cavity, in a tooth. Such curable compounds are generally available in a semi-solid state, and are manipulated and positioned on the surface or in the gap as desired, and hardened or cured into a more solid state for permanency. Curing or hardening is generally a chemical polymerization process which is promoted and driven by various curing conditions and factors. For example, a semi-solid compound or component thereof, may be cured by exposure to air or to energy, such as heat or light energy.

Today, many adhesive and filling compounds are cured by exposure to light energy, particularly visible light energy. The light curing process involves directing a beam of light, such as visible light, at a specific wavelength or band of wavelengths onto a semi-solid light-curable compound to cure the compound. The compound includes light sensitive, chemical components therein which, when exposed to light at the specific wavelength, generally polymerize to harden the compound onto the work surface to bond, fill, or coat the surface.

Specifically, light-curable compounds are widely used in dental procedures. Dentists use light-curable compounds for tooth repairs in a variety of applications including a base, a liner, a coating, a surface seal, a filling for caries and cavities, and to secure crowns or similar dental structures to a tooth surface. Generally, visible light in the blue range of the light spectrum will be sufficient to cure most commonly used dental compounds. Once cured, the dental compound functions, for example, to reduce further tooth decay, to bond dental structures, and/or to provide additional structural support to a tooth.

Generally, curing is effected by various instruments or devices capable of generating visible light and directing this light onto a tooth surface containing the light-curable compound. The light penetrates into the compound layer on the tooth surface for complete curing. The duration of the exposure to light for proper curing of the compound layer depends upon the light-curable compound itself, thickness of the compound layer, and the power and characteristics of the blue light emitted from the curing light instrument. For example, curing a compound to provide a thin tooth surface coating or veneer will require less light energy, while curing a compound to provide a thicker, deeper filling for gaps, such as caries and cavities, will require a greater amount of light energy.

A variety of proposals have previously been made to improve dental curing light devices, which deliver visible light to the tooth. For example, U.S. Pat. No. 7,182,597 to Gill et al. discloses a small, hand-held, self-contained curing light instrument, which efficiently and effectively cures light-curable compounds by maximizing the amount of light directed onto the light-curable compound. The Gill et al. '597 device comprises a hand-held curing light instrument, which includes battery-powered light emitting device and a light guide projecting from a distal end that transmits and directs the generated light to the treatment area. The instrument further includes an electronic control circuit, which controls the time the radiation generated by the light emitting device is emitted, and may further control other factors related to the emission of curing light. The light emitting device emits the light necessary to cure the light-curable compound.

While prior art proposals have greatly advanced the efficiency and effectiveness of curing light instruments, they continue to exhibit a number of drawbacks. Presently, the completion of any dental procedure involving a light-curable compound typically requires a dentist to first use an air-water syringe attached to the chair side dental delivery system to dry the treatment area. After drying the treatment area, the air-water syringe is placed back in the chair side delivery system. The dentist then applies an adhesive layer. Next, the dentist again picks up the air-water syringe to spread and shape the adhesive layer with compressed air. The air-water syringe is again placed back in the chair side delivery system and the Curing light is picked tip, turned on, and the light is applied to the treatment area to cure the light-curable adhesive compound.

The use of such dental delivery systems is inherently problematic with regard to dental procedures involving light-curable compounds. The use of light-curable compounds in dental applications requires a dry and clean operating environment and treatment area. Any water or oil contaminants introduced into the treatment area will reduce the bond strength and increase the risk for failure of the restoration. Dental delivery systems typically operate with the use of an engine driven compressor. Air and water are delivered to the chair through the same tubing. Thus, the probability of oil from the compressor or residual water in the lines reaching the proposed treatment area is high. These contaminants can cause bond failure.

Thus, there is a need to provide an improved curing light instrument to cure compounds in a faster, more efficient, and effective manner. Accordingly, it is desirable to provide a curing light instrument having an integral, self-contained compressed-air system, which allows the dentist to complete a dental procedure involving the use of light-curable compounds using a single hand-held instrument.

It is also desirable to provide a curing light instrument, which provides a controlled blast of clean, dry air, and eliminates the possibility of contamination of oil and water into the bonding environment of the treatment area.

It is further desirable to provide an improved curing light instrument having an integral, self-contained compressed-air system, which further includes an inter-changeable light guides incorporating a variety of air nozzle configurations, which supply controlled blasts of clean, dry air to the treatment area.

SUMMARY OF THE INVENTION

The present invention overcomes many of the disadvantages of prior art providing a hand held curing light device having an integral, self-contained compressed-air system, which allows the operator to complete a procedure involving the use of light-curable compounds using a single hand-held instrument. The self-contained compressed-air system of the present invention includes a replaceable or rechargeable compressed-air cylinder or cartridge that is specifically designed to fit the dental device and keep it operational over the long-term.

The curing light device includes multiple configurations of light guide air nozzles to tailor the device to each particular treatment session. The light and air systems of the present invention may be used separately or in conjunction with one another to efficiently complete the curing of the light-sensitive compound. Further, the present invention includes a method for cure adhesive compounds in a faster, more efficient, and effective manner, while improving convenience and reducing size and overall costs.

By incorporating an integral, self-contained compressed-ail system into the design of a light curing instrument, the subject invention not only eliminates the risk of water and oil contamination in the treatment area, but also streamlines the treatment by reducing the number of times an operator has to put down or pick up different tools during the procedure. The curing light device of the present invention further provides a method to cure compounds in a faster, more efficient, and effective manner, while improving convenience and reducing size and overall costs.

BRIEF DESCRIPTION OF THE DRAWINGS

A more complete understanding of the method and apparatus of the present invention may be had by reference to the following detailed description when taken in conjunction with the accompanying drawings, wherein:

FIG. 1b is an internal perspective view of the embodiment of the improved curing light device of the present invention shown in FIG. 1a;

FIG. 2a is an internal view of the housing of the embodiment of the improved curing light device of the present invention shown in FIG. 1a;

FIG. 2b is a cross-sectional view of the embodiment of the improved curing light device of the present invention shown in FIG. 1a;

Figure 1A:
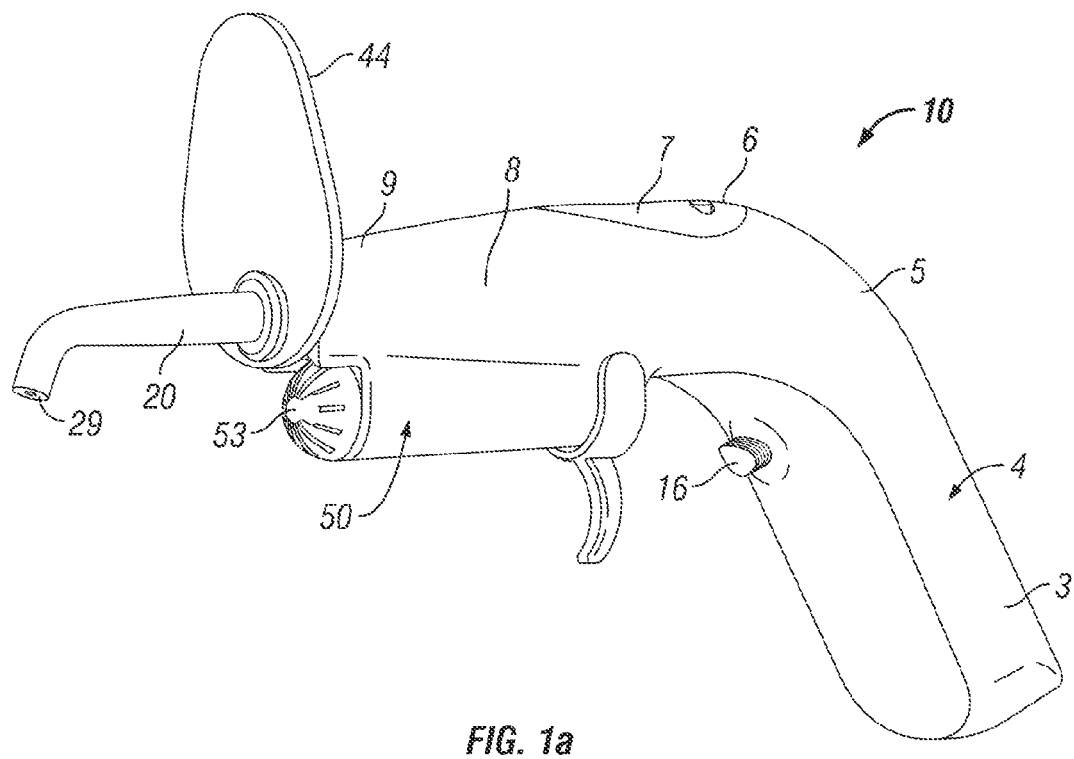
FIG. 1a is a perspective view of an embodiment of the improved curing light device of the present invention.

Where used in the various figures of the drawing, the same numerals designate the same or similar parts. Furthermore, when the terms "top," "bottom." "first," "second," "upper," "lower," "height," "width," "length," "end," "side," "horizontal," "vertical," and similar terms are used herein, it should be understood that these terms have reference only to the structure shown in the drawing and are utilized only to facilitate describing the invention.

All figures are drawn for ease of explanation of the basic teachings of the present invention only; the extensions of the figures with respect to number, position, relationship, and dimensions of the parts to form the preferred embodiment will be explained or will be within the skill of the art after the following teachings of the present invention have been read and understood. Further, the exact dimensions and dimensional proportions to conform to specific force, weight, strength, and similar requirements will likewise be within the skill of the art after the following teachings of the present invention have been read and understood.

DETAILED DESCRIPTION OF THE INVENTION

The present invention provides curing light devices with an integral, self-contained compressed-air system, which allows the dentist to more efficiently and effectively complete a dental procedure involving the use of light-curable compounds using a single hand-held instrument. While the invention will be described in one embodiment herein as having application to curing dental compounds, it is not so specifically limited. Also, the curing light device illustrated herein is portable, however, the invention is not so limited and could alternatively be plugged into a source of power. Portability, of course, provides added convenience of use.

Figure 1B:
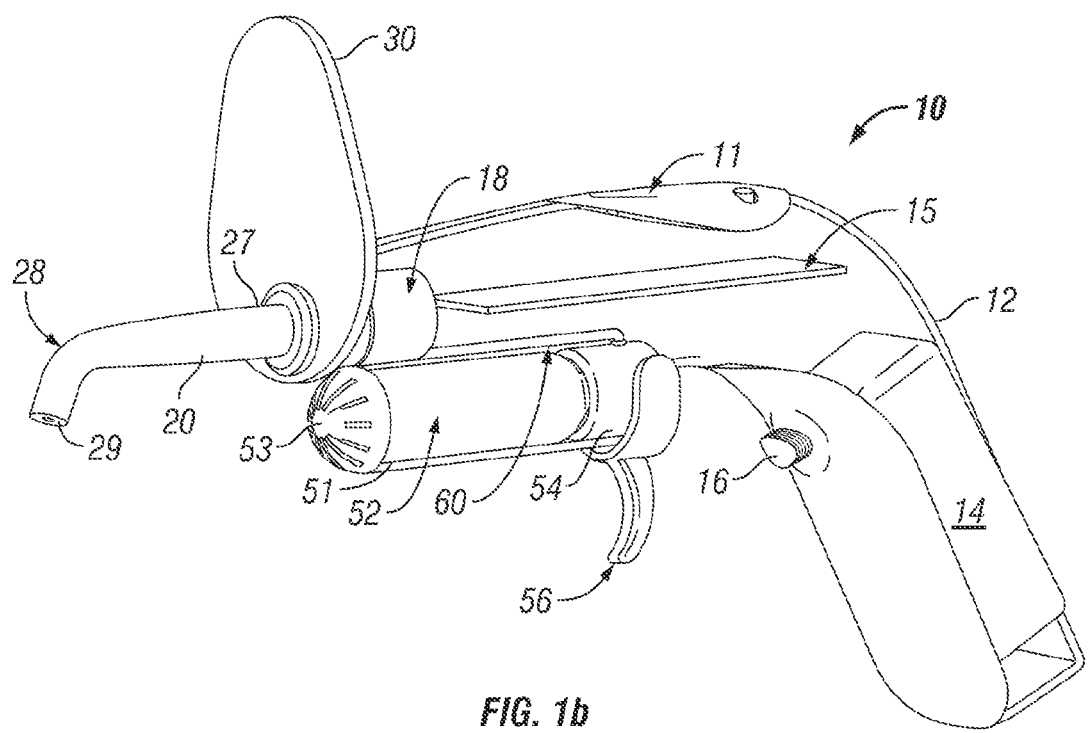

FIGS. 1a and 1b illustrate one embodiment of the curing light device of the present invention. As shown, the curing light device 10 comprises a housing 12, a light emitting device 18 positioned within the housing 12, and light guide air nozzle 20 configured within a adapter socket 40 that interfaces with the light emitting device 18 so as to capture light emitted from the light emitting device 18 and direct it onto a light-curable compound to cure the compound. Advantageously, the curing light device 10 of the present invention further includes an integral, self-contained compressed-air system 50 for selectively supplying controlled blasts of clean, dry air onto the treatment area.

As depicted in FIGS. 1a and 1b, the housing 12 of device 10 is generally a gun-shaped structure having a barrel portion 8 coupled to a handle portion 4. Barrel portion 8 of housing 12 generally includes a distal end 9 and a proximal end 6. Handle portion 4 of housing 12 generally includes a distal end 5 and a proximal end 3. Proximal end 6 of the barrel portion 8 is generally a continuation in structure of the distal end 5 of the handle portion 4. The barrel portion 8 will typically house the light emitting device 18.

The housing 12 of device 10 further includes a socket or opening 51 for receiving a compressed-air cylinder 52. The compressed-air cylinder may be rechargeable or replaceable. As depicted in the Figures, the compressed-air cylinder 52 is configured into the underside of the barrel portion 8. It is understood that the compressed-air cylinder 52 may alternatively be configured on the top of the barrel portion 8 or in the handle portion 4 of the housing 12 of device 10. When properly configured in socket 51 the device 10, the compressed-air cylinder 52 is fixably attached to a valve mechanism 54, which regulates the flow of compressed air out of cylinder 52. In one embodiment, the air cylinder 52 is rotatively attached to the valve mechanism 54. Depleted air cylinders are replaced by simply unscrewing the depleted air cylinder from the valve mechanism 54 and replacing it by screwing in a fully-charged compressed-air cylinder. Alternatively, depleted cylinders may also be recharged.

The valve mechanism 54 is selectively actuated by a trigger mechanism 56. As depicted in the Figures, the trigger mechanism 56 is configured so as to be easily reached by an operator's index finger when holding the pistol-grip handle portion 4 of device 10. By pulling the trigger mechanism 56, the valve mechanism 54 is actuated releasing compressed air from the air cylinder 52. In one embodiment, the valve mechanism 54 is a spring-biased valve mechanism, which allows more air to be released in response to greater pressure being applied to the trigger mechanism 56 and closes automatically when pressure is released from the trigger mechanism 56 mechanism. The valve mechanism 54 fluidly connects the outlet of the compressed-air cylinder 52 with an air supply line 60. As will be shown in greater detail below, the supply line 60, in turn, is in fluid communication with the distal tip 29 of light guide air nozzle 20. Thus, by pulling the trigger mechanism 56, the valve mechanism 54 is opened, which releases a blast of compressed air via supply line 60 to the distal tip 29 of light guide air nozzle 20.

The housing 12, including the barrel portion 8 and the handle portion 4, may be composed of any suitable materials, such as those typically used in the art. Particularly useful are lightweight compact flame resistant materials, such as plastic. In addition, either or both of the barrel portion 8 and handle portion 4 of the housing 12 may be vented for purposes of dissipating heat generated by light emitting device 18. It is particularly beneficial to vent that portion which houses tile light emitting device 18. However, the socket or opening 51 for receiving a compressed-air cylinder 52 is typically insulated or isolated from any venting which dissipates heat generated by light emitting device 18.

The light emitting device 18 is capable of emitting light 30 having wavelengths suitable to cure a light-curable compound. Advantageously, the light emitting device 18 may emit a narrow wavelength band of radiation or light sufficient to cure the compound. In one embodiment, the light emitting device 18 comprises a light emitting diode (LED) type device. In another embodiment, the light emitting device 18 comprises an array of electrical dies. The light emitting device 18 may further include a reflector element, which focuses the emitted light prior to being directed via the light guide air nozzle 20 onto a light-curable compound to cure. The light emitting device 18 may also include filtering devices to filter undesired wavelengths of broad spectrum light. The light emitting device 18 may further include a lens mechanism focusing the emitted light. The light emitting device 18 may also include a forced-air cooling system such as a fan (not shown).

A printed circuit board 15 generally serves to relay the necessary electrical energy, generally through electrical leads, to the light emitting device 18 to generate light. The circuit board 15 may also provide cooling for the light emitting device 18. Accordingly, printed circuit board 15 may comprise thermally conductive materials including metals, such as aluminum, copper, silicon and alloys thereof. The printed circuit board 15, and therefore the light emitting device 18, may be supported by the housing 12 via direct attachment.

Figure 2A:
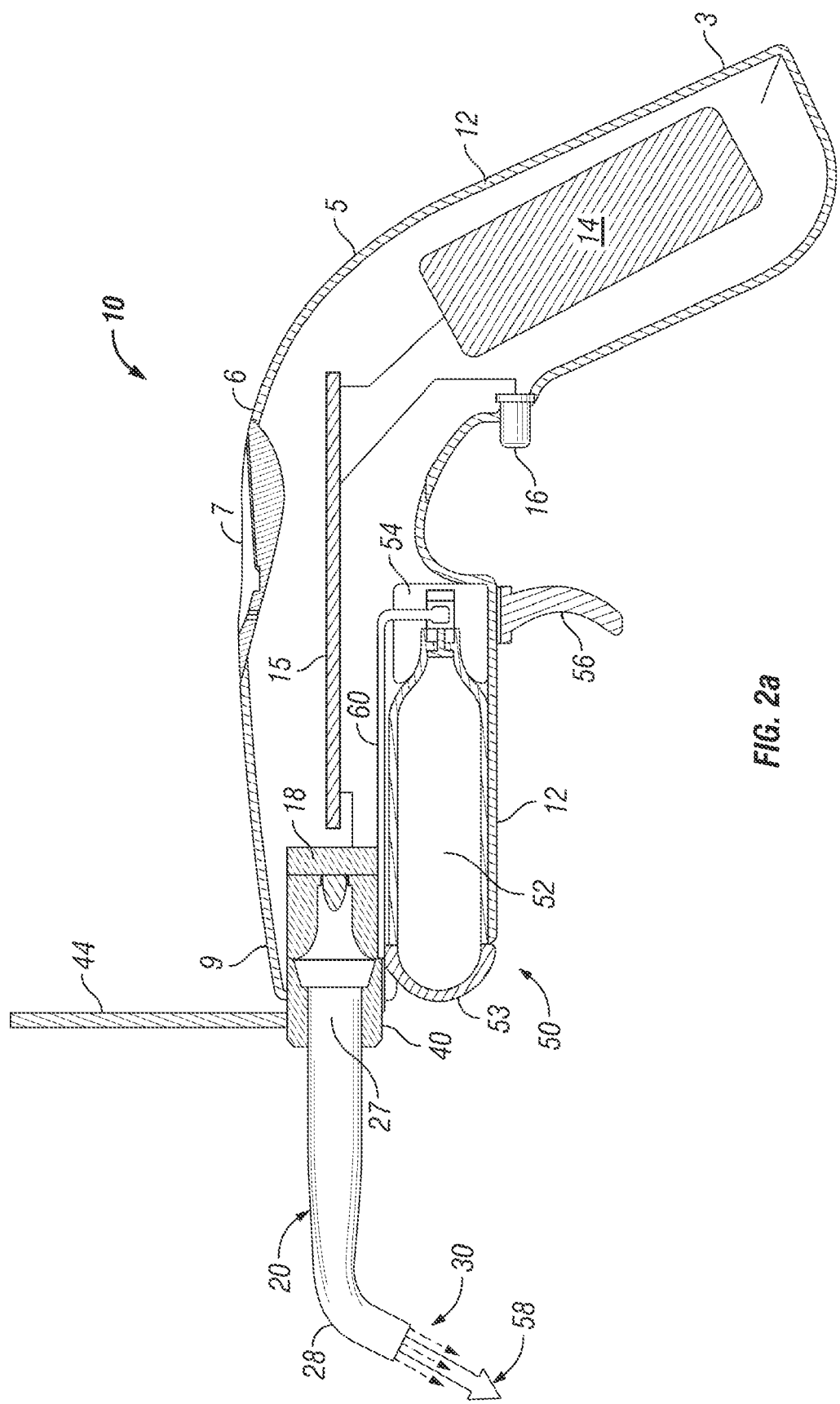

In accordance with the principles of the invention, the light radiated from the light emitting device 18 is efficiently captured and directed for effective curing. For example, as illustrated in FIG. 2*a*, an adapter socket 40, configured near the distal end 9 of the barrel portion 8, interfaces with light emitting device 18. The adapter socket 40 captures the light radiated by the light emitting device 18 and direct it towards a light guide air nozzle 20 projecting from the adapter socket 40. The adapter socket 40 is configured to couple to the proximal end 27 of the light guide air nozzle 20. In this manner, the adapter socket 40 effectively couples light radiated by the light emitting device 18 to the light guide air nozzle 20 so as to provide a continuous interface without a loss of light. Adapter socket 40 may be formed of a lightweight material, such as plastic.

The embodiment of the device 10 illustrated in the FIG. 2*a* includes a light guide air nozzle 20 configured to interface with the adapter socket 40 and to receive and transmit the light 30 and compressed air 58 directed therefrom. The light guide air nozzle 20 generally includes a distal end 28, a distal tip 29 and a proximal end 27, and includes an air delivery tube 26 formed therein which is in fluid communication with air supply line 60 which is connected to the valve mechanism 54.

As shown in the Figures, the light 30 and air 58 are received at the proximal end 27 of the light guide air nozzle 20 also referred to as the receiving end, and transmitted out of (lie distal tip 29 of the light guide air nozzle 20, also referred to as the transmission end. In one embodiment, the proximal end 27 is generally removably secured to the housing 12, or to adapter socket 40. Conventional securing means are suitable. For example, proximal end 27 may be snapped into and out of the distal end 9 of housing 12 or into and out of the adapter socket 40. In addition, light guide air nozzle 20 may be friction fit to the adapter socket 40.

The light guide air nozzle 20 may generally be any shape effective to transmit light. Preferably, the shape of the light guide air nozzle 20 will be adapted for convenience of use depending upon the work surface. For instance, while tile light guide air nozzle 20 may have a relatively uniform diameter from the proximal end 27 through the distal end 28, advantageously, distal end 28 will have a smaller diameter then proximal end 27 to increase the intensity of the exiting light 30 and improve the curing efficiency and convenience of use of the instrument 10. Furthermore, slight bending or tapering of the light guide air nozzle 20 between the distal tip 29 and the proximal end 27 allows the user to cure compounds on work surfaces which would otherwise be difficult to reach. As shown in the Figures, the light guide air nozzle 20 is advantageously tapered proximate the distal end 28.

The light guide air nozzle 20 is comprised of materials and components capable of effectively transmitting light 30. For example, one embodiment of the invention utilizes a light guide air nozzle 20 comprising a plurality of optical fibers (not shown) which are operably fused together into a single light guide or light pipe type stricture to transmit the light 30. In another embodiment, tile light guide air nozzle 20 utilizes a plurality of individual optical fibers or strands which collectively form a conductor. Each strand in the conductor has a taper separate from the taper of each other strand. For example, to form a conductor having individual tapered strands, each of the fiber optic strands may be separately tapered, bundled and fused together to form a solid conductor. The solid conductor may then be stretched to form an elongated stretch section of conical geometry wherein each strand is uniformly tapered over the stretched section. The combined bundle of tapered strands generally imparts a taper to the light guide air nozzle 20. This solid conductor generally has a light receiving end or proximal end 27 and a light transmitting end or distal tip 29 as described above. Further details and additional light guides 52 which are suitable for the present invention are set forth in the U.S. Pat. No. 5,371,826, titled "Dental Fiber Optic Light Bundle with Uniform Taper" and herein incorporated by reference in its entirety.

Figure 2B:
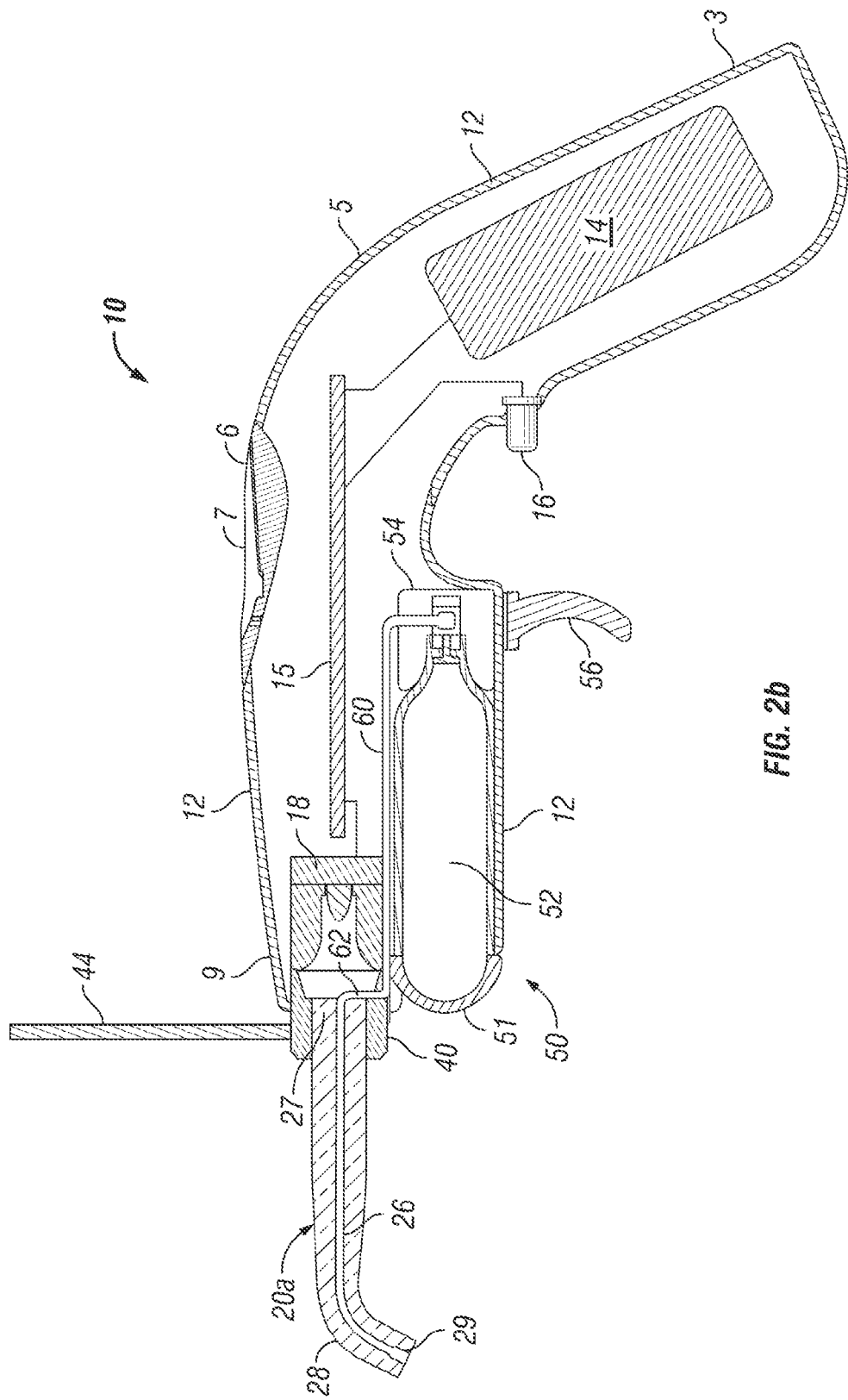

A shield 44 (FIG. 2) may be attached to instrument 10 to protect the operator (not shown) from exposure to light reflected during curing operations. Shield 44 may generally be configured to be easily secured or removably secured to tile light guide air nozzle 20, beneficially to the receiving end 27 of light guide ail nozzle 20. Alternatively, shield 44 may be secured to the distal end 9 of barrel portion 8 of housing 12.

Referring again to in FIGS. 1*a* and 1*b*, the curing light device 10 may also comprise a power source, such as a power supply, to power the curing light instrument 10 and particularly, the light emitting device 18. The power supply may be a portable power supply, such as a battery 14, contained in the housing 12. Advantageously, battery 58 will be a rechargeable battery contained in the handle portion 4 of housing 12. Alternatively, the improved curing light device 10 may be powered by an external source such as an AC power source coupled to a converter to supply DC power to the light emitting device 18. Persons of ordinary skill in the art will readily understand that such an external source may be supplied through an electrical cord (not shown) to the curing light device 10. The power supply is typically coupled to a control circuit on circuit board 15, which controls, regulates, or conditions of the power or electrical energy supplied to the light emitting device 18.

A variety of air-light nozzle configurations are possible with the integral compressed-air system 50 of the curing light device 10 of the present invention. For example, with reference FIG. 2b, in one embodiment the device 10 includes a light guide air nozzle 20, which includes an air delivery tube 26 that is substantially aligned along the longitudinal axis of the light guide air nozzle 20. The air delivery tube 26 extends from the proximal end 27 to the distal tip 29 of the light guide air nozzle 20. The air delivery tube 26 is in direct fluid communication with the air supply line 60. Since the air delivery tube 26 exits in the center of the distal tip 29 of the light guide air nozzle 20, the operator can simply "point and shoot" compressed air in a manner nearly identical to how the cure light is activated.

Figure 3A:
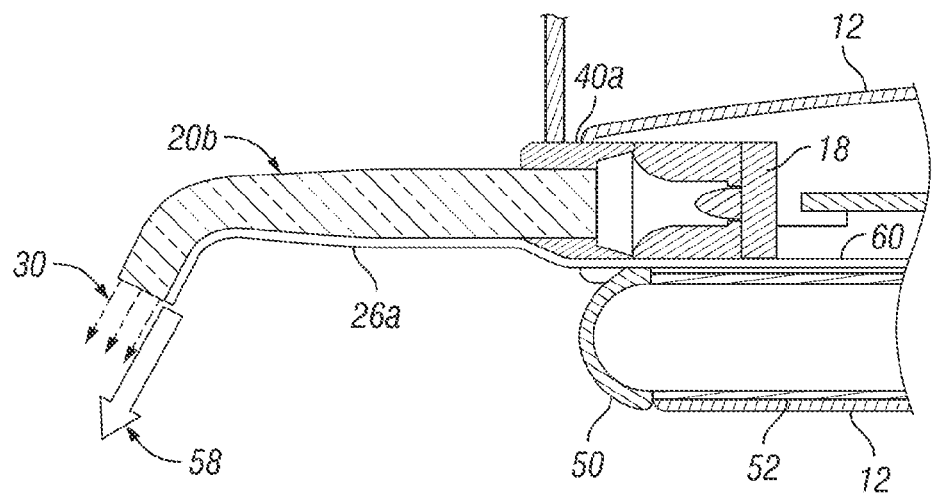
FIG. 3a is a magnified cross-sectional view of all alternate embodiment of barrel portion of the housing of improved curing light device of the present invention.

In the embodiment depicted in FIG. 3a, the air supply line 60 extends through an adapter socket 40a and is aligned along the bottom of a conventional light guide 20b. The air delivery tube 26a follows the contours of the light guide 20b before discharging the compressed air at the distal tip 29 of light guide air nozzle 20b.

Figure 3B:
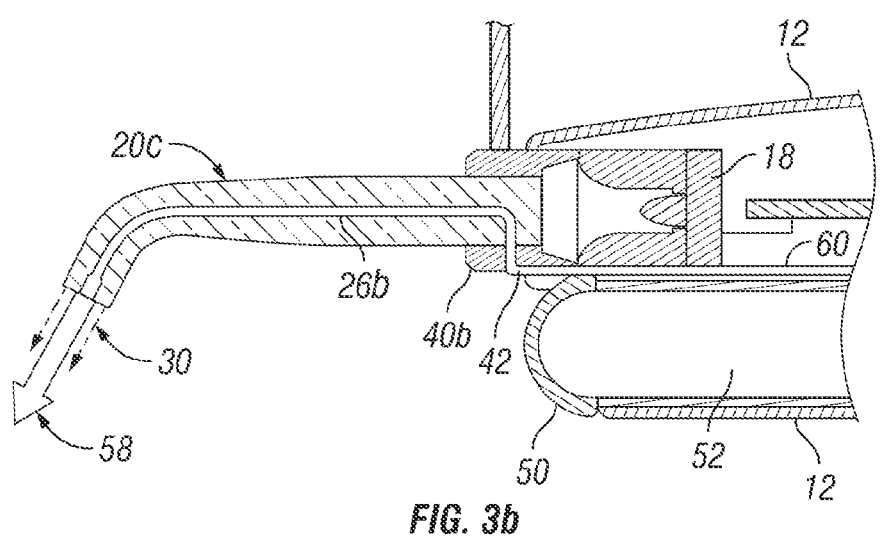
FIG. 3b is a magnified cross-sectional view of another embodiment of barrel portion of the housing of improved curing light device of the present invention and FIG. 3c is a magnified cross-sectional view of another embodiment of barrel portion of the housing of improved curing light device of the present invention.
Figure 3C:
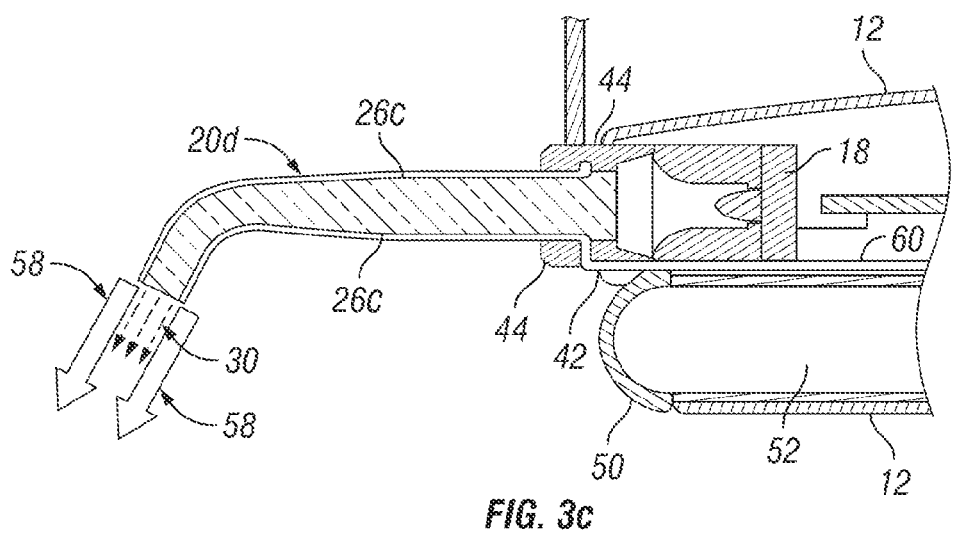

With reference now to FIGS. 3b and 3c, another embodiment of the device is shown. Each of the depicted embodiments include an alternate embodiment of the adapter socket 40b, which includes a passageway 42 formed therein. The passageway 42 enables the air supply line 60 to connect to air delivery tubes formed in a wide variety of interchangeable light guide air nozzles. For example, in FIG. 3b, when air light guide air nozzle 20c is properly aligned and secured within adapter socket 40b, passageway 42 fluidly connects the air delivery tube 26b formed therein with the air supply line 60, which is fluidly connected to the valve mechanism 54 of the compressed-air system 50. As depicted in the Figure, the air delivery tube 26b tube is substantially aligned along the longitudinal axis of the light guide air nozzle 20 and extends from the distal tip 29 to the near the proximal end 27 of the light guide air nozzle 20. However, instead of exiting out the proximal tip of light guide air nozzle 20c, the air delivery tube 26b exits through the outer circumference of the light guide air nozzle 20c.

In FIG. 3b, the light guide air nozzle 20d comprises an air delivery tube 26c which is aligned with the longitudinal axis and configured about the periphery of the light transmitting material forming an annulus about the light guide element. When the air light guide air nozzle 20d is properly aligned and secured within adapter socket 40b, passageway 42 fluidly connects the air delivery tube 26c formed about the light guide air nozzle 20d with the air supply line 60. This results in air 58 being channeled to the outer periphery of the distal tip 29 of the light guide air nozzle 20d.

The embodiments illustrated in the Figures further allow the operator to easily control the timing requirements of light 30 and air 58 emitted. As shown, a trigger switch 16, which may be located in the handle portion 4 of the housing 12, is generally used to power the light emitting device 18. Likewise, the trigger mechanism 56 of the integral compressed-air system 50 is configured so as to be easily reached by an operators index finger when holding the pistol-grip handle portion 4 of device 10.

Trigger switch 16 is electrically coupled to the control circuit on the circuit board 15 and controls the ON/OFF function of light 30 emitted from the light emitting device 18. Further switches (not shown) may also be located in the housing 12, for example in the handle portion 4, to control other aspects of the emission of curing light 30. For instance, instrument 10 may have a second switch (not shown) designed to control the power flowing to the light emitting device 18 and/or to regulate the level or power of the radiation emitted. In such an instrument, these control switches would also be coupled to control circuit on the circuit board 15 to allow the operator complete control over all aspects necessary to properly cure the compound. In addition, housing 12 may further include an LCD display 7 to display relevant information concerning the operation of the device 10.

The present invention also provides a method to complete the curing of light-curable compounds. While the method refers to curing compounds used in dental applications, the invention is not so limited. Generally, the operator, a dentist for example, dries the treatment area by positioning the curing light device 10 of the present invention in proximity to the treatment area and pulling the trigger mechanism 56 of the integral compressed-air system 50. Pulling the trigger mechanism 56 actuates the valve mechanism 54 allowing compressed air to flow from the air cylinder 52 to the distal tip of the light guide air nozzle 20 via air supply line 60. After drying the treatment area, the dentist then applies a layer light-curable adhesive compound to the treatment area. The dentist again positions the curing light device 10 of the present invention in proximity to the compound. The operator grips the instrument 10 at the handle portion 17 of housing 12 and directs the light transmitting end, typically the distal tip 29 of the light guide air nozzle 20 towards the treatment area (not shown), such as a tooth. The operator then activates the curing light instrument 10 by adjusting and/or depressing the trigger switch 16 appropriately to generate light, or turn ON light 30, to begin to cure a light-curable compound. The light emitting device 18 emits light 30 having the desired power and wavelength to cure the compound. In addition, the operator can also shape the compound by intermittently pulling the trigger mechanism 56 of the integral compressed-air system 50 to release a blast of compressed air at the treatment site. The trigger mechanism 56 of the integral compressed-air system 50 is independent from the trigger switch 16 of the light generating device 20 and vice-versa. Thus, both the light and air systems may be used separately or in conjunction with one another to efficiently complete the curing of the light-sensitive compound. Once the operator is satisfied that tile compound has been sufficiently shaped and cured, the curing light may be turned OFF by simple release of the trigger switch 16.

Thus, the invention provides a small, compact, durable, and portable curing light and integral compressed-air system for prepping, shaping and curing light-curable materials used in dental applications. Also, the portable nature of the device allows the operator to carry the instrument and use as needed.

Although the invention hereof has been described by way of preferred embodiments, it will be evident that other adaptations and modifications can be employed without departing from the spirit and scope thereof. For example, the trigger and valve mechanism of the compressed-ail system could also be electrically actuated and controlled. The terms and expressions employed herein have been used as terms of description and not of limitation; and thus, there is no intent of excluding equivalents, but on the contrary it is intended to cover any and all equivalents that may be employed without departing from the spirit and scope of the invention.

I claim:

1. A device for curing light-curable compounds, comprising:
   a hand-held housing;
   a light emitting device configured in said housing, wherein when activated, said light emitting device emits light having wavelengths suitable to cure a light-curable compound;
   a light guide air nozzle extending from said housing, said nozzle consisting of a single unitary light transmitting structure that includes a proximal end, which captures light emitted from the light emitting device, and a distal tip, which receives said captured emitted light transmitted through said structure and projects said light onto a light-curable compound to cure the compound; wherein said light transmitting structure includes an integral tubular passageway formed therein that is aligned substantially along the longitudinal axis of the light transmitting structure and extends through the distal tip;
   a compressed-air delivery system configured in said housing, said system comprising a compressed-air cylinder connected to a valve mechanism, said valve mechanism is connected to an air supply tube which is fluidly connected to said tubular passageway, wherein said valve mechanism selectively and fluidly connects the compressed-air cylinder with the distal tip of said light guide air nozzle when said valve mechanism is actuated.

2. The device of claim 1 wherein said compressed-air cylinder is replaceable.

3. The device of claim 1 wherein said compressed-air cylinder is rechargeable.

4. The device of claim 1 further comprising an adapter socket configured in said housing and dimensioned for receiving the proximal end of said light guide air nozzle in one end and interfacing with said light emitting device on an opposing end.

5. The device of claim 4 wherein said adapter socket further includes a second passageway which fluidly connects said supply tube with said tubular passageway.

6. The device of claim 1, further comprising a trigger mechanism attached to said valve mechanism, wherein said trigger mechanism selectively actuates said valve mechanism.

7. The device of claim 1, wherein said tubular passageway is substantially aligned parallel with the longitudinal axis of the light guide air nozzle.

8. The device of claim 1, wherein said light guide air structure is tapered from the proximal end to distal tip.

9. The device of claim 1, wherein the air delivery tube is substantially co-aligned with the longitudinal axis of the light transmitting structure.

10. The device of claim 1, wherein the light emitting device comprises a light emitting diode.

* * * * *

UNITED STATES PATENT AND TRADEMARK OFFICE
CERTIFICATE OF CORRECTION

| | |
|---|---|
| PATENT NO. | : 8,366,441 B2 |
| APPLICATION NO. | : 12/350207 |
| DATED | : February 5, 2013 |
| INVENTOR(S) | : Mary K. Swift |

It is certified that error appears in the above-identified patent and that said Letters Patent is hereby corrected as shown below:

Column 6, line 59, delete "tile" and insert --the--.
Column 8, line 51, delete "tile" and insert --the--.

Signed and Sealed this
Second Day of April, 2013

Teresa Stanek Rea
*Acting Director of the United States Patent and Trademark Office*